United States Patent
Narath et al.

(10) Patent No.: US 6,214,780 B1
(45) Date of Patent: *Apr. 10, 2001

(54) ENHANCED PROCESSING OF SYNTHETIC BAR COMPOSITIONS COMPRISING AMPHOTERICS BASED ON MINIMAL LEVELS OF FATTY ACID SOAP AND MINIMUM RATIOS OF SATURATED TO UNSATURATED SOAP

(75) Inventors: William Narath, Parsippany; Gregory Ornoski, Cliffside Park, both of NJ (US); James Corr, Dix Hills, NY (US)

(73) Assignee: Lever Brothers Company, division of Conopco, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,145

(22) Filed: Mar. 8, 2000

(51) Int. Cl.$^7$ ....................................... A61K 7/50
(52) U.S. Cl. .................. 510/152; 510/155; 510/156; 510/447
(58) Field of Search ................................... 510/141, 152, 510/155, 156, 447

(56) References Cited

U.S. PATENT DOCUMENTS

| | | |
|---|---|---|
| 2,894,912 | 7/1959 | Geitz . |
| 4,663,070 * | 5/1987 | Dubrovolny et al. ................ 252/121 |
| 4,695,395 * | 9/1987 | Caswell et al. ....................... 252/121 |
| 5,372,751 | 12/1994 | Rys-Cicciari et al. . |
| 5,494,612 | 2/1996 | Finucane . |
| 5,510,050 | 4/1996 | Dunbar et al. . |
| 5,520,840 | 5/1996 | Massaro et al. . |
| 5,656,579 | 8/1997 | Chambers et al. . |
| 5,661,120 * | 8/1997 | Funucane et al. .................... 510/153 |
| 5,683,973 | 11/1997 | Post et al. . |
| 5,780,405 | 7/1998 | He et al. . |
| 5,795,852 | 8/1998 | He et al. . |
| 5,916,856 * | 6/1999 | Massaro et al. ...................... 510/141 |

* cited by examiner

*Primary Examiner*—Necholus Ogden
(74) *Attorney, Agent, or Firm*—Ronald A. Koatz

(57) ABSTRACT

The present invention relates to synthetic bar compositions comprising amphoteric surfactants (e.g., betaine) in which, by using floor levels of fatty acid soap and floor ratios (minimum amounts) of saturated to unsaturated soap, enhanced processing (i.e., measured as rates of extrusion) is obtained at higher levels of amphoteric.

11 Claims, No Drawings

ENHANCED PROCESSING OF SYNTHETIC BAR COMPOSITIONS COMPRISING AMPHOTERICS BASED ON MINIMAL LEVELS OF FATTY ACID SOAP AND MINIMUM RATIOS OF SATURATED TO UNSATURATED SOAP

FIELD OF THE INVENTION

The present invention relates to synthetic soap bar compositions comprising amphoteric surfactants (i.e., for enhanced mildness) which surprisingly can be readily processed, even at relatively high levels of amphoteric (i.e., above 1%). Processability is measured as enhanced throughput, measured as bars plod in pounds per minute. Specifically, the invention relates to bar compositions comprising anionic (e.g., acyl isethionate), amphoteric and fatty acid soap (introduced as a mixture of various chain length fatty acid soaps or as a single chain length soap) wherein amphoteric-containing bars (normally extremely difficult to extrude when used at levels above 1% by weight) are readily processed by using minimal levels of fatty acid soap and minimal ratios of saturated to unsaturated soap.

BACKGROUND

Traditionally, soap has been used as a skin cleanser. While soap is low in cost, easy to manufacture and lathers well, it is also very harsh on skin.

In order to alleviate the harshness of soap, synthetic bars have been used in which much of the soap is replaced with milder surfactants, e.g., acyl isethionates. Patents relating to the use of acyl isethionate and soap, therefore, are known (see U.S. Pat. No. 2,894,912 to Geitz).

It is also known to make bars which are even milder by replacing soap, isethionate or fatty acid (used primarily as structurant) with very mild surfactants such as amphoteric surfactants. Normally, however, it is extremely difficult to successfully and economically process bars containing both mild anionics and amphoterics (e.g., betaine).

U.S. Pat. No. 5,372,751 to Rys-Cicciari et al. does teach bar compositions comprising anionic (e.g., acyl isethionate) and betaine. The reference notes at several points that soap is preferably absent (column 6, lines 60–61; column 9, line 47) and this is confirmed by examples where soap is never used in amounts greater than 2%. While the reference suggests this is done for reasons of mildness, applicants have also previously never been able to process amounts of betaine above 1% at these low levels of soap.

Unexpectedly, applicants have found that when minimal levels of fatty acid soap (e.g., 3% and up) are used in bars comprising an anionic surfactant system, much greater levels of amphoteric (2% and up) can be readily processed than previous possible.

Applicants have further discovered that when the total content of saturated soap to unsaturated soap is greater than 1:1, process benefits (e.g., rate of plodding) are enhanced yet further. At the same time, the ability to successfully process more betaine allows introduction of much greater mildness benefit.

BRIEF SUMMARY OF THE INVENTION

In one embodiment of the invention, the invention relates to bar compositions comprising:

(a) 10% to 70% anionic surfactant (e.g., fatty acyl isethionate);

(b) 2% to 15%, preferably 2% to 10%, more preferably 3% to 8% amphoteric surfactant;

(c) 3% to 25%, preferably 5% to 15% of a fatty acid soap comprising a mixture of $C_6$ to $C_{24}$ fatty acids or a single $C_6$ to $C_{24}$ fatty acid soap;

wherein ratio of saturated fatty acid soap to unsaturated fatty acid soap is greater than 1:1, preferably greater than 2:1, preferably greater than 5:1 and more preferably greater than 10:1. Indeed, the fatty acid "mixture" of fatty acids may comprise 100% saturated fatty acids (i.e., no unsaturated fatty acids at all).

That is, by ensuring minimum levels of soap (3% and up) and minimum levels of saturated fatty acid, strong processing benefits (e.g., enhanced plodding rates) are achieved. Without minimum soap levels only very low levels of amphoteric (i.e., about 1% or less) can be efficiently processed and plodded. Minimum levels of saturation enhances plodding rates and zein rates even further.

DETAILED DESCRIPTION OF THE INVENTION

The present invention relates to synthetic based (e.g., anionic based) soap bar compositions comprising amphoteric surfactants (and/or zwitterionic surfactants) wherein, based on minimum levels of soap (i.e., 3% and up), it has become unexpectedly possible to efficiently process much greater amounts of said amphoteric and/or zwitterionic surfactant than previously possible.

That is, although the benefit of using amphoteric/zwitterionic surfactant has been previously recognized (e.g., for enhanced mildness), these surfactants make the products soft and sticky. Thus, it has been difficult to process (i.e., stamp and extrude) synthetic bars containing such surfactants. Unexpectedly, applicants have discovered that one reason the processing may have been so difficult is because such amphoteric/zwitterionics have been previously used in synthetic bars substantially free of soap (i.e., having about 2% or less soap). Unexpectedly, however, applicants have found if the amphoteric/zwitterionic is used in a synthetic structured bar wherein the level of soap is about 3% and up (i.e., a 3% to 25% soap), the zwitterionic/amphoteric becomes much more readily processable. Thus, it now becomes possible to use much greater quantities of zwitterionic/amphoteric than previously possible while processing at efficient/economic rates (e.g., greater than 5 lbs./minute based on a pilot plant extruder).

In a second embodiment, applicants have found that increasing the level of saturated to unsaturated fatty acid increases processing even further. Specifically, where levels of saturates to unsaturates is greater than 1:1, enhanced processing is achieved.

Specific components of the invention are discussed in greater detail below.

Anionic

The bar compositions of the invention comprise 10% to 70% anionic surfactant or mixture of anionic surfactants.

Preferably, the bar compositions comprise about 10% to 70% by weight fatty acyl isethionate.

The acyl isethionate, if used, has the formula:

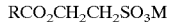

wherein R is alkyl or alkenyl group of 6 to 21 carbons and M is a solubilizing cation such as sodium, potassium, ammonium or substituted ammonium.

These esters are generally prepared by the reaction between alkali metal isethionate and mixed aliphatic fatty acids having from, for example, 6 to 18 carbons and iodine value of less than 20.

The anionic surfactant may also be an ether sulphate of the formula

where $R_1$ is alkyl or alkenyl of 8 to 18 carbon atoms, especially 11 to 15 carbon atoms, y has an average value of at least 1.0 and M is a solubilizing cation such as sodium, potassium, ammonium or substituted ammonium. Preferably y has an average value of 2 or more.

Other anionic detergents may be used. Possibilities include alkyl glyceryl ether sulphates, sulphosuccinates, taurates, sarcosinates, sulphoacetates, alkyl phosphates and acyl lactates. Sulphosuccinates may be monoalkyl sulphosuccinates having the formula:

$$R^2O_2CCH_2CH(SO_3M)CO_2M;$$

and amido-MEA sulphosuccinates of the formula:

$$R^2CONHCH_2CH_2O_2CCH_2CH(SO_3M)CO_2M;$$

wherein $R^2$ ranges from $C_8$–$C_{20}$ alkyl, preferably $C_{12}$–$C_{15}$ alkyl and M is a solubilizing cation.

Sarcosinates are generally indicated by the formula $$R^3CON(CH_3)CH_2CO_2M,$$

wherein $R^3$ ranges from $C_8$–$C_{20}$ alkyl, preferably $C_{12}$–$C_{15}$ alkyl and M is a solubilizing cation.

Taurates are generally identified by the formula $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilizing cation.

Mildness Enhancing Surfactant

The second component of the bar composition of the invention is a mildness enhancing surfactant which may be a zwitterionic surfactant, amphoteric surfactant or mixtures thereof.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2\text{---}Y^{(+)}\text{---}CH_2\text{---}R^4Z^{(-)}$$
$$(R^3)_x$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups. Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6, 9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

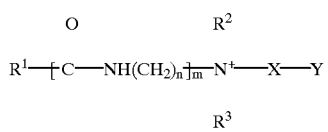

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

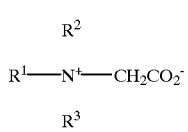

and amido betaines of formula:

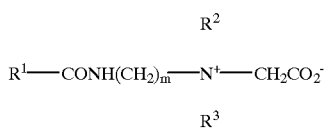

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

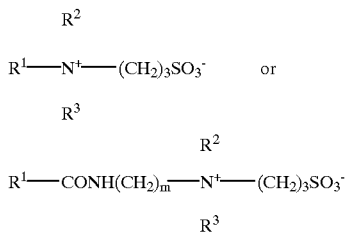

where m is 2 or 3, or variants of these in which —$(CH_2)_3SO^-_3$ is replaced by

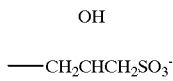

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises about 2% to 20% by weight, preferably 2% to 10%, more preferably 3% to 8% by wt. of the composition.

The ratio of anionic to zwitterionic/amphoteric may vary broadly and may be from 2:1 to 50:1, preferably 5:1 to 20:1.

Soap

A third required component of the subject invention is soap component (e.g., alkali metal fatty acid component).

The soaps are generally introduced as a mixture of longer and shorter, saturated and unsaturated fatty acids.

Generally, the longer chain soaps predominate the mixture and may comprise, for example, 30 to 100% (e.g., where all are longer chain, e.g., $C_{16}$ and $C_{18}$) of the mixture while short chains may comprise 0 to 40%; however, it should be noted that shorter chain may predominate if divalent or trivalent cations (e.g., magnesium, calcium) are used.

Preferably, the mixture comprises mostly $C_8$ to $C_{18}$ and preferably $C_{12}$ to $C_{18}$, more preferably $C_{16}$ $C_{18}$. Generally, it is known that longer chain soaps are more mild.

The soaps useful herein are the well known alkali metal salts of natural or synthetic aliphatic (alkanoic or alkenoic) acids having about 6 to 24 carbon atoms, preferably 8 to 18 carbon, more preferably about 12 to about 18 carbon atoms. They may be described as alkali metal carboxylates having about 6 to about 24 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats and oils. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucumoil, cohune nut oil, murumuru oil, jaboty kernel oil, khakan kernel oil, dika nut oil, and ucunhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided. Indeed, as noted below, saturation is preferred.

Soaps may be made by the classic kettle boiling process or modern continuous soap manufacturing processes wherein natural fats and oils such as tallow or coconut oil is their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

A second way in which the soap may be introduced is, not as soap (blends) described above, but simply as an alkali metal or alkanol ammonium salt of alkane or alkene $C_{12}$–$C_{14}$, preferably $C_{16}$–$C_{20}$ monocarboxylic acid. An example of this includes sodium stearate.

It is a critical aspect of the invention that the soap must comprise at least about 3% by wt. (e.g., 3% to 25%, preferably 5% to 15% by wt.) of the bar composition. Previous art has not appreciated that minimal soap quantities are needed to efficiently and economically process bars comprising zwitterionic/amphoterics, particularly when the amphoteric/zwitterionics (e.g., betaine) are used at higher and higher levels. That is, as levels of zwitterionic/amphoteric up to 2% and up, minimum 3% soap levels are required.

In a second embodiment of the subject invention, applicants have found that processing is further enhanced by increasing ratio of saturated to unsaturated soap.

While not wishing to be bound by theory, it is believed that increasing level of saturation provides better structure to bar due to more effective crystallization.

Specifically, applicants have found that where the level of saturated soap to unsaturated soap is 1:1 or greater, preferably 2:1 and up; more preferably 10:1 and up, processing (plodding rates) is enhanced. Further, mildness is either enhanced or is not compromised.

Optional

While anionic surfactant, e.g., acyl isethionate, is required, as well as an amphoteric/zwitterionic surfactant, other surfactants may also be used.

Among these are included nonionics and cationics.

Nonionic surfactants include in particular the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference and polyhydroxyamides such as described in U.S. Pat. No. 5,312,954 to Letton et al., hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Volume I & II) by Schwartz, Perry & Berch, both of which are also incorporated into the subject application by reference.

Free fatty acids of 8–22 carbon atoms may also be desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8–18, preferably 10–16, in an amount up to 35% by weight of the composition. Skin feel and creaminess enhancers, the most important of which is stearic acid, are also desirably present in these compositions.

Skin mildness improvers also preferably used in the composition of the invention are salts of isethionate. Effective salts cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolammonium or tri-ethanolammonium ions.

Particularly preferred as a mildness improver is simple, unsubstituted sodium isethionate of the general formula wherein R is hydrogen.

The skin mildness improver will be present from about 0.5% to about 50%. Preferably, the mildness improver is present from about 1% to about 25%, more preferably from about 2% to about 15%, optimally from 3% to 10%, by weight of the total composition.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated,. Illustrative of this type additive are salts selected from the group consisting of alkali metal and organic amine higher aliphatic fatty alcohols sulfates, alkyl aryl sulfonates, and the higher aliphatic fatty acid taurinates.

Adjunct materials including germicides, perfumes, colorants, pigments such as titanium dioxide and water may also be present.

The following examples are intended to be illustrated only and are not intended to limit the invention in any way.

Ingredients

The following is a breakdown of the saturated fats (bold) and unsaturated fats (not bold) of various soaps used in the examples.

TABLE 1

Saturated/Unsaturated Levels in Soaps [1,2]

| FATTY ACID | COCONUT SOAP | BEEF TALLOW SOAP | SODIUM STEARATE |
|---|---|---|---|
| Caproic | 0.2 | — | — |
| Caprylic | 8.0 | — | — |
| Capric | 7.0 | — | — |
| Lauric | 48.2 | — | — |
| Myristic | 17.3 | 2.2 | — |
| Palmitic | 8.8 | 35.0 | 55.0 |
| Stearic | 2.0 | 15.7 | 45.0 |
| Oleic | 6.0 | 44.4 | — |
| Linoleic | 2.5 | 2.2 | — |
| Linolenic | — | 0.4 | — |
| Arachidonic | — | 0.1 | — |

[1] Saturated Soaps are in Bold Print

[2] 82/18 Neat Soap is a blend of Sodium Tallowate and Sodium Cocoate.

The following formulations are used in both zein tests and plodding tests.

Control

| Ingredient | % by Weight | Range |
|---|---|---|
| Sodium Cocoyl Isethionate | ≈50% | 40–60% |
| Stearic Acid (e.g., C8 to C24 fatty acid) | ≈20% | 10–30% |
| Fatty Acid Soap Blend (e.g., 82/18) | ≈8% | 5–12% |
| Sodium Stearate | ≈3.0% | 1–5% |
| Betaine | — | — |
| Coconut Fatty Acid | ≈3.0% | 1–5% |
| Sodium Isethionate | ≈5.0% | 3–7% |
| Sodium Dodecyl Benzene Sulfonate | ≈2.0% | 1–5% |
| Fragrance, Dyes, Preservatives | ≈1.7% | 0.5–5% |
| Water | ≈5.0% | 1–10% |

TABLE 1

Formulations for Control and Experimental Formulations for Patent Application for Betaine (All formulation changes are in BOLD).

| Ingredient | Control | EXP1 | EXP2 | EXP3 | EXP4 | EXP5 | EXP6 | EXP7 | EXP8 |
|---|---|---|---|---|---|---|---|---|---|
| Sodium Cocoyl Isethionate | 49.78 | 49.78 | 49.78 | 49.78 | 49.78 | 49.78 | 49.78 | 49.78 | 49.78 |
| Stearic Acid | 20.13 | 20.13 | 20.13 | 20.13 | 20.13 | 20.13 | 20.13 | 13.13 | 13.13 |
| 82/18 Neat Soap | 8.31 | 10.00 | 0.00 | 8.00 | 0.00 | 6.00 | 0.00 | 10.00 | 0.00 |
| Sodium Stearate | 2.98 | 0.00 | 10.00 | 0.00 | 8.00 | 0.00 | 6.00 | 0.00 | 10.00 |
| Betaine | 0.00 | 3.0 | 3.0 | 5.00 | 5.00 | 7.00 | 7.00 | 10.00 | 10.00 |

TABLE 1-continued

Formulations for Control and Experimental Formulations for Patent Application for Betaine (All formulation changes are in BOLD).

| Ingredient | Control | EXP1 | EXP2 | EXP3 | EXP4 | EXP5 | EXP6 | EXP7 | EXP8 |
|---|---|---|---|---|---|---|---|---|---|
| Coconut Fatty Acid | 3.08 | 3.08 | 3.08 | 3.08 | 3.08 | 3.08 | 3.08 | 3.08 | 3.08 |
| Sodium Isethionate | 4.68 | 4.68 | 4.68 | 4.68 | 4.68 | 4.68 | 4.68 | 4.68 | 4.68 |
| Vista C560 Slurry | 2.02 | 0.00 | 0.00 | 0.00 | 0.00 | 0.00 | 0.00 | 0.00 | 0.00 |
| Tetrasodium EHDP | 0.02 | 0.02 | 0.02 | 0.02 | 0.02 | 0.02 | 0.02 | 0.02 | 0.02 |
| Tetrasodium EDTA | 0.02 | 0.02 | 0.02 | 0.02 | 0.02 | 0.02 | 0.02 | 0.02 | 0.02 |
| Sodium Chloride | 0.35 | 0.35 | 0.35 | 0.35 | 0.35 | 0.35 | 0.35 | 0.35 | 0.35 |
| Titanium Dioxide | 0.15 | 0.15 | 0.15 | 0.15 | 0.15 | 0.15 | 0.15 | 0.15 | 0.15 |
| BHT | 0.0075 | 0.0075 | 0.0075 | 0.0075 | 0.0075 | 0.0075 | 0.0075 | 0.0075 | .0075 |
| Fragrance | 1.0 | 1.0 | 1.0 | 1.0 | 1.0 | 1.0 | 1.0 | 1.0 | |
| Miscellaneous | 2.53 | 2.53 | 2.53 | 2.53 | 2.53 | 2.53 | 2.53 | 2.53 | 2.53 |
| Water | 5.25 | 5.25 | 5.25 | 5.25 | 5.25 | 5.25 | 5.25 | 5.25 | 5.25 |

EXP 1: Control with 3% Betaine, 10% 82/18 Neat Soap
EXP 2: Control with 3% Betaine, 10% Sodium Stearate
EXP 3: Control with 5% Betaine, 8% 82/18 Neat Soap
EXP 4: Control with 5% Betaine, 8% Sodium Stearate
EXP 5: Control with 7% Betaine, 6% 82/18 Neat Soap
EXP 6: Control with 7% Betaine, 6% Sodium Stearate
EXP 7: Control with 10% Betaine, 10% 82/18 Neat Soap
EXP 8: Control with 10% Betaine, 10% Sodium Stearate Zein Testing Mildness Assessments Zein dissolution test was used to preliminarily screen the irritation potential of the formulations studied. In an 8 oz. jar, 30 mLs of an aqueous dispersion of a formulation were prepared. The dispersions sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

EXAMPLES 1 to 7

In order to show effect of increasing saturation on bars (by using more sodium stearate, which is 100% saturated soaps, versus 82/18 soap, which is mixture, saturation is increased), applicants tested compositions with varying levels of betaine (3%, 5%, 7% and 10%) with either 82/18 soap or sodium stearate and the results are set forth in Table 2 below.

Zein Results on Mildness Formulations

| Formulation | Example | % Zein |
|---|---|---|
| Control | Comparative | 46.6 |
| Control with 3% Betaine 10% 82/18 Neat Soap | 1 | 42.7 |
| Control with 3% Betaine 10% Sodium Stearate | 2 | 39.8 |
| Control with 5% Betaine 8% 82/18 Neat Soap | 3 | 36.4 |
| Control with 5% Betaine 8% Sodium Stearate | 4 | 34.1 |
| Control with 7% Betaine 6% 82/18 Neat Soap | 5 | 34.7 |
| Control with 7% Betaine 6% Sodium Stearate | 6 | 32.3 |
| Control with 10% Betaine 10% 82/18 Neat Soap | 7 | 42.1 |
| Control with 10% Betaine 10% Sodium Stearate | 8 | 37.5 |

Free Fatty Acid was constant throughout all formulations except for examples 7 and 8.

As can be clearly seen, every time sodium stearate was substituted for "neat" soap (i.e., indication of more saturation), zein scores (indication of mildness, i.e., lower the zein score, the milder the bar) were lowered. Thus, use of saturates clearly enhanced mildness.

Processing

In order to show use of higher saturates also enhanced processing, the same examples 1–7 were fed to a chip mixer, refiner and plodder to determine extrusion rates and results are set forth in Table 3 below:

| Formulation | Experiment | Refiner (lbs/min.) Chips to Noodles[1] (lb/min) | Refiner (lbs/min.) Noodles to Noodles[2] (lb/min) | Plodder[3] (lbs/min) |
|---|---|---|---|---|
| Control | Control | 6.3 | 7.7/10.6 | 10.6 |
| Control with 3% Betaine 10% 82/18 Neat Soap | 1 | 6.9 | 7.2/9.1 | 9.4 |
| Control with 3% Betaine 10% Sodium Stearate | 2 | 7.9 | 7.5/10.1 | 13.0 |
| Control with 5% Betaine 8% 82/18 Neat Soap | 3 | 7.4 | 8.9/7.9 | 9.2 |
| Control with 5% Betaine 8% Sodium Stearate | 4 | 7.8 | 7.9/11.8 | 11.4 |
| Control with 7% Betaine 6% 82/18 Neat Soap | 5 | 4.6 | 5.7/— | 7.3 |
| Control with 7% Betaine 6% Sodium Stearate | 6 | 7.3 | 6.4/9.3 | 8.0 |
| Control with 10% Betaine 10% 82/18 Neat Soap | 7 | 4.7 | 2.3/3.1 | 1.5 |
| Control with 10% Betaine 10% Sodium Stearate | 8 | 5.6 | 5.3/6.9 | 8.7 |

[1]Refining of Chips to noodles: refiner operating at 9 rpms.
[2]Refining of noodles to noodles: refiner operating at 9 and 14 rpms, data supplied is (lb/min @ 9 rpms/(lb/min) @ 14 rpms)
[3]Plodding of logs: refiner at 14 rpms, plodder at 14 rpms.

It can again be clearly seen, that substituting stearate for neat soap mixtures enhanced extrusion rates.

Moreover, what should be especially noted is that levels of betaine (i.e., 2% and up) could be efficiently processed (e.g., >5 lbs/min). Applicants have previously been unable to obtain such rates at these levels of betaine. Only upon discovery that minimum levels of soap were needed was it possible to achieve these efficient rates.

What is claimed is:

1. A mild bar composition comprising:
   (a) 40–60% by wt. of an anionic surfactant, anionic surfactants or mixtures thereof;
   (b) 2% to 15% by weight of a zwitterionic and/or amphoteric surfactant; and
   (c) 3% to 25% by wt. of a fatty acid soap;
   wherein said fatty acid soap comprises a mixture of $C_8$ to $C_{18}$ chain length saturated and optionally unsaturated fatty acids;
   wherein said saturated fatty acids are selected from the group consisting of at least caproic, caprylic, capric, lauric, myristic, palmitic, stearic and mixtures thereof;
   wherein said unsaturated fatty acids are selected from the group consisting of at least oleic, linoleic, arichidonic, and mixtures thereof;
   wherein the ratio of saturated fatty acid soap to unsaturated fatty acid soap is greater than 1:1 and wherein said mildness is defined by low Zein scores.

2. A composition according to claim 1, wherein the anionic is isethionate of formula $RCO_2CH_2CH_2SO_3M$; wherein R is $C_7$ to $C_{21}$ alkyl or alkenyl group and M is a solubilizing cation.

3. A composition according to claim 1, wherein anionic is alkyl glyceryl ether sulfate.

4. A composition according to claim 1, wherein anionic is acyl isethionate.

5. A composition according to claim 1, wherein amphoteric has formula

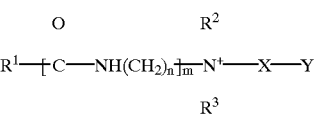

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$.

6. A composition according to claim 1, wherein amphoteric is amide betaine of formula:

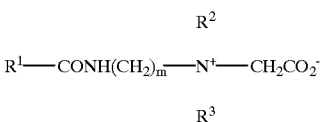

where m is 2 or 3.

7. A composition according to claim 1, wherein amphoteric/zwitterionic comprises 2% to 10% by wt. of the composition.

8. A composition according to claim 7, wherein amphoteric comprises 3% to 7% by wt. of the composition.

9. A composition according to claim 1, wherein the amount of fatty acid soap $C_{16}$ chain length and higher comprises 30% to 100% of total fatty acid soap and the amount of fatty acid soap $C_6$ to $C_{14}$ chain length comprises 0% to 40% of total fatty acid soap.

10. A composition according to claim 1, wherein the fatty acid soap comprises $C_8$ to $C_{18}$ chain length.

11. A composition according to claim 1, where fatty acid soap comprises 5 to 15% by wt. of the composition.

* * * * *